United States Patent [19]

Hunter

[11] Patent Number: 4,479,516
[45] Date of Patent: Oct. 30, 1984

[54] ELECTRICALLY DRIVEN TOOTHBRUSH

[76] Inventor: Frank M. Hunter, c/o Nunyara Medical Center, Church St., Terrigal, Austria, 2260

[21] Appl. No.: 346,779

[22] Filed: Feb. 8, 1982

[51] Int. Cl.³ .......................................... A45D 44/18
[52] U.S. Cl. ................................. 132/84 R; 132/11 A
[58] Field of Search ................ 132/84 R, 11 A, 11 R; 433/130, 133

[56] References Cited

U.S. PATENT DOCUMENTS

| | | | |
|---|---|---|---|
| 1,824,398 | 9/1931 | Fleischhacker | 433/130 |
| 3,159,859 | 12/1964 | Rasmussen | 132/11 R UX |
| 3,204,469 | 9/1965 | Spillers | 132/11 R |
| 3,439,422 | 4/1969 | Doeden et al. | 433/133 |
| 3,459,199 | 8/1969 | Connell | 132/11 R |
| 3,474,795 | 10/1969 | Hantman et al. | 132/11 R |
| 3,509,629 | 5/1970 | Kidokoro et al. | 433/133 |
| 3,533,421 | 10/1970 | Mays | 132/11 A |
| 4,056,111 | 11/1977 | Mantelet | 132/11 A |
| 4,275,749 | 6/1981 | Caroli | 132/11 A |
| 4,292,986 | 10/1981 | Ergaver | 132/11 R |
| 4,295,829 | 10/1981 | Martinelli | 433/133 |

*Primary Examiner*—Gregory E. McNeill
*Attorney, Agent, or Firm*—Christie, Parker & Hale

[57] ABSTRACT

An electrically driven toothbrush comprising a casing (2) for use as a handle which supports an electric motor (10) a motor reversing means (4) and a speed reducing means (26,18); a stem (46) extending from the handle with a brushhead at one end of the stem, the rotary motion of the stem being in use continuous until reversed by manual operation of the motor reversing means (4). Another version has no motor reversing means and has an oscillating brushhead (74) driven by a slotted roller (70) and an eccentric pin (74) on a shaft (78) within the stem (46).

6 Claims, 4 Drawing Figures

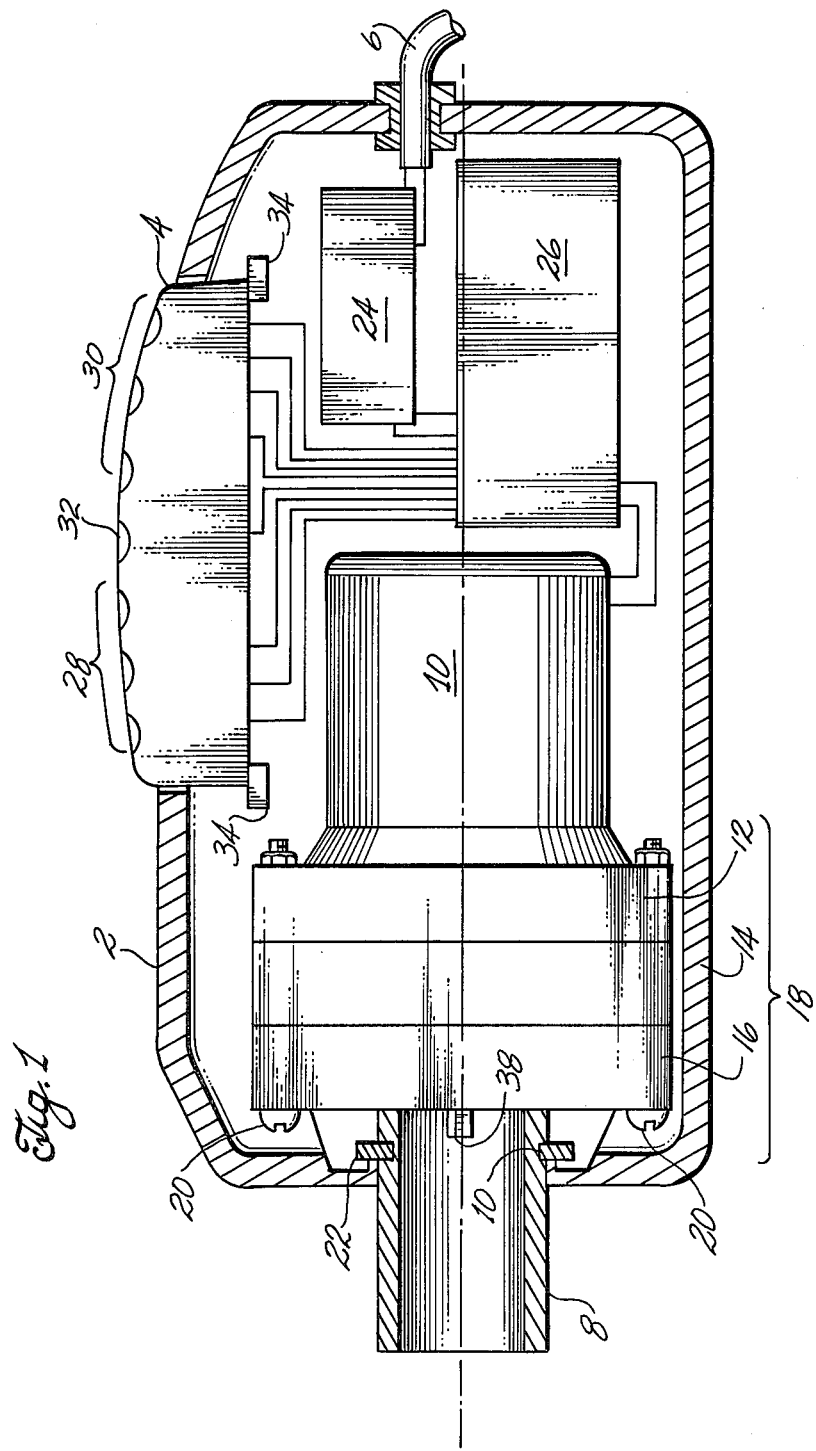

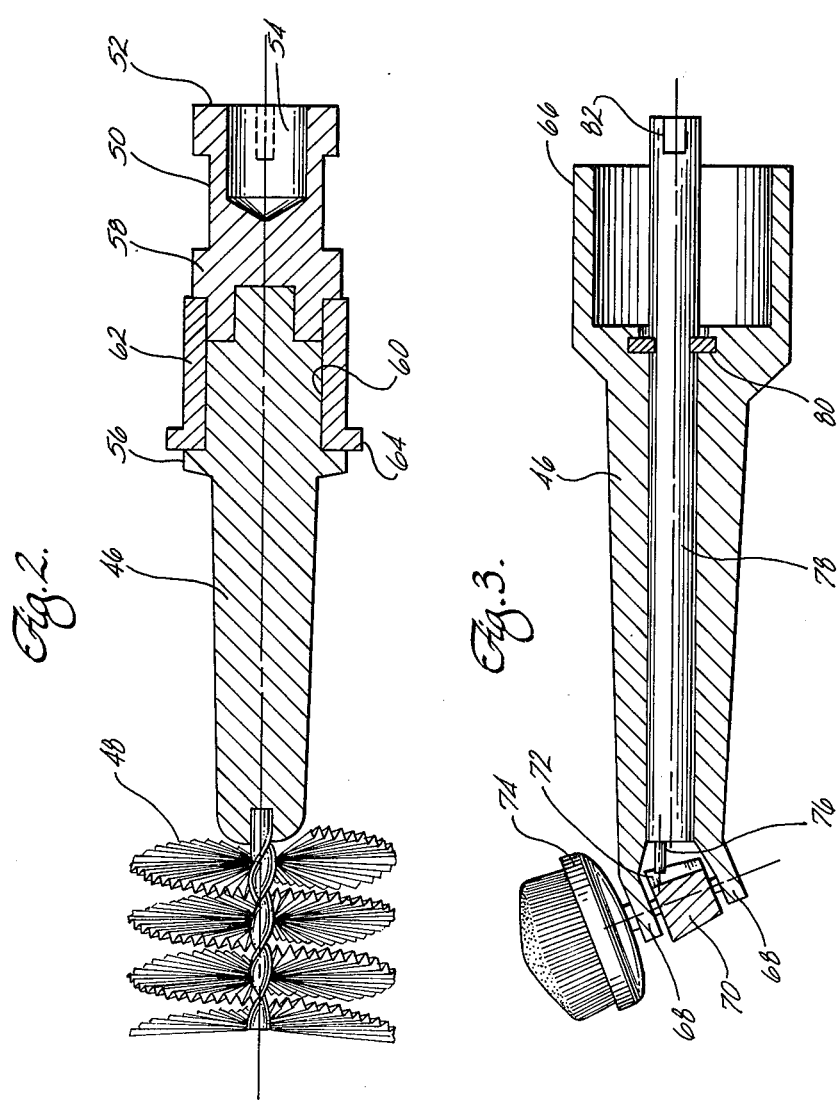

ELECTRICALLY DRIVEN TOOTHBRUSH

This invention concerns electric toothbrushes.

BACKGROUND OF THE INVENTION

Various theories regarding the care of teeth have from time to time held sway as to the correct mode and consequently methods of cleaning the teeth have evolved in order to practise the theory. For many years it has been recommended that a hand held brush should be used with a circular motion for efficient enamel cleaning, food removal and a gum massage. Recently such advice was thought to be a compromise between what was best and what adults and children could be expected to perform daily.

I have shown that a sweeping motion with brush bristles over the gum toward the teeth in a direction substantially perpendicular to the gum results in improved overall hygiene because the border between the gum and enamel is swept unidirectionally so as to seal the region of overlap instead of separating the gum from the enamel. Such a motion is difficult to carry out by hand moreover the direction of the sweep must be reversed between the upper and lower teeth so as to preserve and promote the sealed attachment in the gingival sulcus between the gingiva and the cemento-enamel junction. The application of such sweeping motion requires both patience and persistence and is much more conveniently formed by a powered brush.

SUMMARY OF THE INVENTION

This invention provides an electrically driven toothbrush comprising a stationary handle part which supports an electric motor, a motor reversing means and a speed reducing means; a stem extending from the handle part a head at one end of the stem with an array of bristles extending from the head, and the stem imparts rotary motion to the head, the rotary motion imparted by the stem being continuous until reversed manually with the motor reversing means.

In another version the invention provides an electrically driven toothbrush comprising a stationary handle part which supports an electric motor, a motor reversing means and a speed reducing means; a stem which extends from the handle part one end being drivable rotationally by the motor, the opposite end having a radial array of bristles.

In yet another version the invention provides an electrically driven toothbrush comprising a stationary handle part which supports an electric motor, a speed reducing means; a stem extending from the handle part, a head with an array of bristles extending therefrom supported at one end of the stem for rotational movement, drive means supported by the stem, and drivable by the motor and in driving connection with the head for producing oscillating motion of the head. Preferably the speed reducing means is a gearbox driven by the motor and there is between the gearbox and the stem a coupling affording releasable driving connection to interchangeable stems. The speed reducing means may be an electronic circuit which changes the motor speed stepwise. The gearbox may have two different output speeds and a coupling capable of engagement by the stem or the drive means driven by the stem in two different modes whereby speed selection is obtainable. Preferably the gearbox is an epicyclic gearbox with a carrier plate which is rotatable at one speed and a coaxial sun gear shaft which revolves at the other speed for any given motor speed, the carrier plate and shaft constituting one half of the coupling the remaining half of the coupling being constituted by the driven end of the stem or the driven end of the drive means supported by the stem, those halves incorporating interfitting conformations. In a preferred form the carrier plate has a central splined aperture and the coaxial sun gear shaft has a splined end; the driven end of the stem having a tubular socket with an outer surface provided with axial splines complementary to the aperture splines and a cavity which receives the splined end of the shaft but does not contact the shaft. Conveniently the handle part has a stem supporting collar situated coaxially with the base of the stem and the stem has a sleeve bearing situated adjacent the tubular socket, the outer surface of the sleeve bearing being a push fit within the collar. The carrier plate may have a central splined aperture and the coaxial sun gear shaft may have a splined end; the stem may be a tube which is a push fit upon a collar extending from the handle part, the drive means may be a drive shaft supported for rotation in the stem tube one end of which has a socket with interior splines which are complementary to the splines on the sun gear shaft the other end of which drive shaft has a pin and slot connection with the head for producing oscillating motion of the head.

DESCRIPTION OF THE DRAWINGS

An embodiment of the invention with interchangeable stems is now described with reference to the drawings in which FIG. 1 is a diagrammatic part sectional view of the handle part;

FIG. 2 is a sectional side elevation of one form of stem and brush;

FIG. 3 is a sectional side elevation of another form of stem;

DETAILED DESCRIPTION

Figure 4:
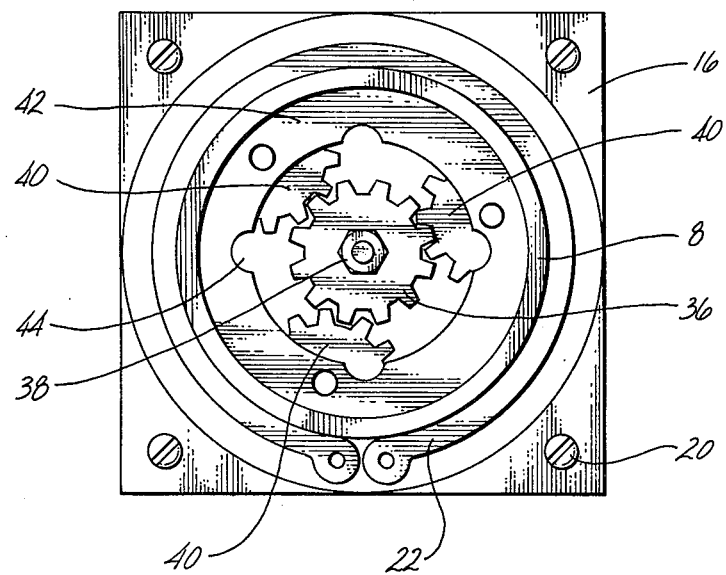
FIG. 4 is a view from direction A of the gearbox when removed from the handle part to show the manner of coupling the stems.

The handle part consists of a moulded plastic casing 2 having a switch aperture for a switch assembly 4; a cable aperture for a power flex 6; a stem aperture for a brass collar 8. A 6 volt, 4.2 watt D.C. motor 10 drives three stages 12, 14, 16 of an epicyclic gearbox jointly indicated as 18. The stages of the gearbox are connected in axial alignment by bolts 20. The brass collar 8 extends into stage 16 of the gearbox and is positioned by airclip 22. The cable 6 supplies 12 v AC current from a transformer pack (not shown) adapted to be plugged directly into a mains power point or receptacle. Circuit board 24 rectifies the current in a standard rectifier circuit. Circuit board 26 in conjunction with switch assembly 4 permits the user to select three forward speeds by operation of one of the bridge-contact switches of group 28 and three reverse speeds by operation of one of the switches of group 30. The motor is stopped and started with switch 32. These items are standard circuitry. Moulded ledges 34 support switch assembly 4.

Each stage of the gearbox has a sun and planet gears with the planet gears driving a carrier plate which drives the input gear of the next stage in known manner. The third stage 16 is different because it must impart drive to both versions of the stem shown in FIGS. 2 and 3, at a ratio to suit the particular brush head selected by the user. Stage 12 achieves a step down of 6:1 and stage 14 likewise giving an overall reduction ratio of 36:1 corresponding to 440 rpm which is the speed of sun pinion 36 and hexagonal shaft 38 of FIG. 4. Stage 16 is a step up stage of 1:4 which means that three planet pinions 40 and carrier plate 42 revolve faster at an overall reduction of 9:1. Carrier plate 42 has splines 44 which impart slow drive to the stem shown in FIG. 2. The hexagonal shaft 3 imparts fast drive to the stem shown in FIG. 3.

Referring now to FIG. 2, the nylon stem 46 supports a spiral brush 48 at one end and at the opposite end is secured to a nylon socket 50 fitted with moulded splines 52 complementary to splines 44 on the carrier plate. Cavity 54 is of sufficiently large diameter to clear hexagonal shaft 38. The socket and stem together define a pair of opposed shoulders 56, 58 defining between them a bearing surface 60 surrounded by a brass flanged sleeve 62 the outer diameter of which is a push fit into the interior of collar 8 to an extent determined by flange 64. This limits the reach of socket 50 toward the carrier plate 42 while allowing the two to couple.

Referring now to FIG. 3, the hollow stem 46 widens at one end into a tube 66 which is a push fit onto the outside of collar 8. The head end of the stem is shaped to form a pair of snap fit bearings 68 which support a tapered nylon roller 70 with an axial slot 72. Brush 74 lies at an obtuse angle to the axis of the stem. Oscillating motion is imparted to roller 70 by an eccentric metal pin 76 carried by drive shaft 78. The latter is retained in the stem by a clip 80. The end of the shaft 78 opposite the pin 74 is formed as a hexagonal socket 82 which couples with hexagonal shaft 38.

The following output speeds were measured under conditions of average load, the motor speeds being changed by the integrated circuit board 26 in response to finger operation of switch group 28.

| Motor rpm | Stem shaft rpm of radial brush | Stem shaft rpm of oscillating brush |
|---|---|---|
| 15840 | 440 | 1200 |
| 12600 | 350 | 1000 |
| 10800 | 300 | 750 |

While a toothbrush with both types of brush action has been described it is possible to construct versions suited to only one brush action. Thus an oscillating brush action requires no reversing switch.

A variety of interchangeable stems are available providing different bristle hardness, packing and length.

I have found the advantages of the above embodiment to be

1. The interproximal spaces are swept efficiently by the helical brush.
2. The buccal, labial, palatal and lingual tooth surfaces can all be swept in a direction which presses the gingiva onto those surfaces, at the same time massaging the gum area generally.
3. Equal cleaning of the right and left sets is possible whether the user is left or right handed.
4. As the dental and oral condition of users varies considerably, a speed range is of great assistance in offering both plaque control and gingival massage.
5. The speed selection helps considerably in overcoming the apprehension of which users experience in introducing into the mouth a fast, electrically driven instrument. Aged users particularly wish to start on as slow a speed as possible.

I claim:

1. An electrically driven toothbrush comprising a stationary handle part which supports an electric motor, a motor reversing means and a speed reducing means; a stem extending from the handle part a head at one end of the stem with an array of bristles extending from the head, and the stem imparts rotary motion to the head, the rotary motion imparted by the stem being continuous until reversed manually with the motor reversing means, the speed reducing means being a gearbox driven by the motor and there is between the gearbox and the stem a coupling affording releasable driving connection to interchangeable stems, the gearbox being an epicyclic gearbox with a carrier plate which is rotatable at one speed and a coaxial sun gear shaft which revolves at the other speed for any given motor speed, the carrier plate and shaft constituting one half of the coupling, the remaining half of the coupling being constituted by the driven end of the stem or the driven end of the drive means supported by the stem, those halves incorporating interfitting conformations.

2. An electrically driven toothbrush as claimed in claim 1 wherein the carrier plate has a central splined aperture and the coaxial sun gear shaft has a splined end; the driven end of the stem having a tubular socket with an outer surface provided with axial splines complementary to the aperture splines and a cavity which receives the splined end of the shaft but does not contact the shaft.

3. An electrically driven toothbrush as claimed in claim 1 wherein the handle part has a stem supporting collar situated coaxially with the base of the stem and the stem has a sleeve bearing situated adjacent the tubular socket, the outer surface of the sleeve bearing being a push fit within the collar.

4. An electrically driven toothbrush as claimed in claim 1 wherein the carrier plate has a central splined aperture and the coaxial sun gear shaft has a splined end; the stem is a tube which is a push fit upon a collar extending from the handle part, the drive means is a drive shaft supported for rotation in the stem tube one end of which has a socket with interior splines which are complementary to the splines on the sun gear shaft the other end of which drive shaft has a pin and slot connection with the head for producing oscillating motion of the head.

5. An electrically driven toothbrush as claimed in claim 4 wherein the head is disposed at an obtuse angle to the stem and is mounted on a roller supported in a pair of bearings, the roller having an axial slot whereas the drive shaft has an eccentrically mounted pin which engages the slot.

6. An electrically driven toothbrush as claimed in any one of claims 3, 4, or 5 wherein the handle part comprises a substantially tubular hollow casing, the stem supporting collar projecting from one end, entering electric power supply wires and components constituting a speed change circuit board located at the opposite end, the motor and gearbox being housed between the circuit board and the collar and a switch assembly located along the length of the casing.

* * * * *